(12) United States Patent
Song

(10) Patent No.: US 8,329,003 B2
(45) Date of Patent: Dec. 11, 2012

(54) SYSTEM AND METHOD FOR DETECTING AND PREVENTING GALVANIC CORROSION

(75) Inventor: Guangling Song, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 146 days.

(21) Appl. No.: 13/021,812

(22) Filed: Feb. 7, 2011

(65) Prior Publication Data

US 2012/0199495 A1   Aug. 9, 2012

(51) Int. Cl.
*C23F 13/04* (2006.01)
*C23F 13/22* (2006.01)

(52) U.S. Cl. ........ 204/196.06; 204/196.11; 204/196.21; 204/196.24; 204/196.26; 204/196.36; 205/727; 205/730; 205/740

(58) Field of Classification Search ............. 204/196.06, 204/196.11, 196.21, 196.24, 196.26, 196.36; 205/727, 730, 740
See application file for complete search history.

(56) References Cited

U.S. PATENT DOCUMENTS

| | | | | |
|---|---|---|---|---|
| 4,117,345 A | * | 9/1978 | Balcom | 307/95 |
| 4,644,285 A | * | 2/1987 | Britton | 205/726 |
| 4,956,610 A | * | 9/1990 | Galm et al. | 324/425 |
| 6,358,397 B1 | * | 3/2002 | Lyublinski | 205/734 |

* cited by examiner

*Primary Examiner* — Bruce Bell
(74) *Attorney, Agent, or Firm* — Quinn Law Group, PLLC

(57) ABSTRACT

A system for detecting and preventing galvanic corrosion of an anodic metal includes a potential detector configured to monitor an electrical potential within the electrolyte solution, a signal amplifier coupled with the potential detector, and a current delivery circuit coupled with the signal amplifier. The signal amplifier is configured to provide an output proportional to the monitored electrical potential, and the current delivery circuit is configured to provide a current to a cathodic metal that is proportional to the output of the signal amplifier.

20 Claims, 2 Drawing Sheets

SYSTEM AND METHOD FOR DETECTING AND PREVENTING GALVANIC CORROSION

TECHNICAL FIELD

The present invention relates generally to systems and methods for the detection and prevention of galvanic corrosion.

BACKGROUND

Galvanic corrosion is an electrochemical process in which one metal corrodes preferentially to another metal when both metals are in electrical contact and exposed to a continuous electrolyte. Such a configuration is often referred to as a "galvanic couple," and results when each metal has a different electrode potential. Various metals are often ranked according to their electrode potential in the "Anodic Index," with magnesium having a generally more negative potential than steel, steel having a generally more negative potential than copper, and gold having the noblest potential.

In a galvanic couple, the cathode anodically polarizes the anode and accelerates the dissolution of the anode in the electrolyte. This leads to the anodic metal corroding more quickly than it otherwise would, while the corrosion of the cathodic metal is retarded even to the point of stopping.

SUMMARY

A system for detecting and preventing galvanic corrosion of an anodic metal is provided herein. The system may be particularly useful when the anodic metal is provided in a galvanic couple with a cathodic metal and exposed to an electrolyte solution. The system may include a potential detector configured to monitor an electrical potential within the electrolyte solution, a signal amplifier coupled with the potential detector, and a current delivery circuit coupled with the signal amplifier. The signal amplifier may be configured to provide an output proportional to the monitored electrical potential of the solution, and the current delivery circuit may be configured to provide a current to the cathodic metal that is proportional to the output of the signal amplifier. In an embodiment, the signal amplifier may be an inverting signal amplifier.

In a particular arrangement, the potential detector may include a first and second sensory electrode, where each electrode may be configured to electrically contact the electrolyte solution and detect an electrical potential of the solution. The potential detector may be disposed adjacent to the anodic metal, though may have one electrode disposed proximate an edge of the anodic metal. In an embodiment, the second electrode may be disposed more distant from the edge of the anodic metal than the first electrode.

The system may further include a corrosion indicator that may be configured to receive the output of the signal amplifier and to provide an alert if the output is above a threshold. Additionally, the current delivery circuit may include a power amplifier and a current delivery electrode that are electrically coupled with the cathodic metal. Such a system may be operatively configured to detect corrosion of a magnesium-based vehicle wheel.

Additionally, a method of detecting and preventing galvanic corrosion of an anodic metal is also provided. Such a method may be used when the anodic metal is provided in a galvanic couple with a cathodic metal, and exposed to an electrolyte solution. The method may include detecting an electrical potential within the electrolyte solution above a portion of the anodic metal, amplifying the detected electrical potential, and applying a current to the cathodic metal that is proportional to the amplified electrical potential.

The electrical potential within the electrolyte solution may be detected by providing a first electrode adjacent to the anodic metal, providing a second electrode adjacent to the anodic metal and apart from the first electrode, and detecting an electrical potential between the first and second electrodes. The first and second electrodes may each be configured to electrically contact the electrolyte solution, and may be provided in a transverse arrangement to an interface between the anodic and cathodic metals.

If the amplified electrical potential is above a threshold, the method may further include providing an alert that may indicate the potential for corrosion.

The above features and advantages and other features and advantages of the present invention are readily apparent from the following detailed description of the best modes for carrying out the invention when taken in connection with the accompanying drawings.

DETAILED DESCRIPTION

Figure 1:
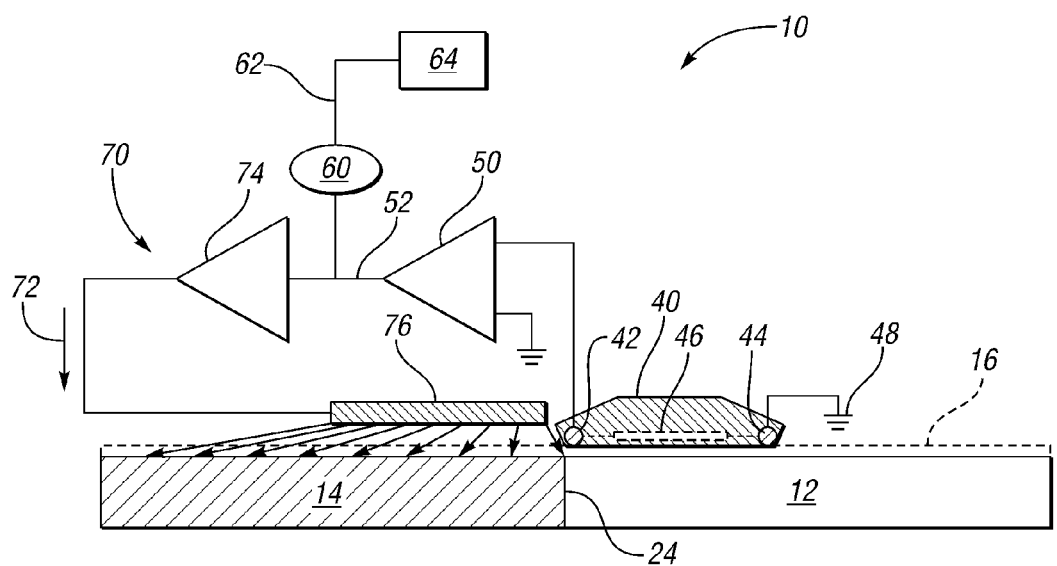
FIG. 1 is a schematic diagram of a system for detecting and preventing galvanic corrosion of an anodic metal.

Referring to the drawings, wherein like reference numerals are used to identify like or identical components in the various views, FIG. 1 schematically illustrates a system 10 for detecting and preventing galvanic corrosion of an anodic metal 12. As generally known in the art, an anodic metal 12 (i.e., an "anode") may have a tendency to corrode when provided in a galvanic couple with a cathodic metal 14 (i.e., a "cathode") and exposed to an electrolyte solution 16.

Figure 2:
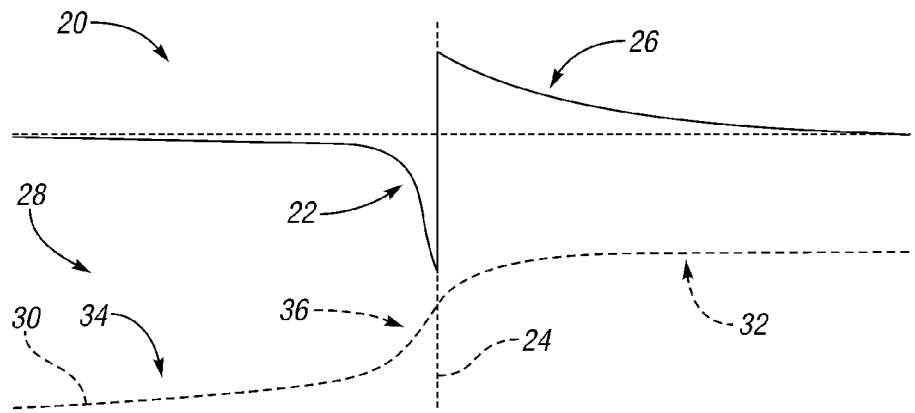
FIG. 2 is a current density plot and electrolyte solution potential plot across the anode and cathode illustrated in FIG. 1, in the absence of a protective current.

In general, the galvanic couple, such as shown in FIG. 1, may cause a current to flow from the anode 12 to the cathode 14 in the electrolyte 16. This current flow across the anode 12 and cathode 14 may be represented on a current density plot 20, as generally illustrated in FIG. 2, where the vertical axis represents the magnitude of the current at a point along the materials. As shown, a negative current density may represent a received current, where a positive current density may represent a supplied current. The magnitude of the current density within the cathode (generally at 22) is the greatest at a point that is immediately proximate to the anode-cathode interface 24. This current density tapers off, however, as a function of distance from the interface 24. Similarly, the magnitude of the current density within the anode (generally at 26) is also the greatest at a point immediately proximate to the interface 24, yet also tapers off as a function of distance from the interface 24.

FIG. 2 further illustrates a plot 28 of the electrical potential 30 of the electrolyte solution 16 across the anode 12 and cathode 14. As generally illustrated, the electrical potential 30 of the solution 16 may be relatively higher above the anodic metal 12 (generally represented at 32) than above the cathodic metal 14 (generally represented at 34). Near the interface 24, however, there may be a transition region (generally represented at 36) where the potential 30 of the solution 16 may transition from the higher anodic potential 32, to the lower cathodic potential 34. Such a transition may be most prominent near the interface 24, however, may also be apparent to a lesser extent away from the interface 24.

Referring again to FIG. 1, the system 10 may include a potential detector 40 that is configured to monitor an electrical potential within the electrolyte solution. The potential detector 40 may include, for example, two electrodes 42, 44 that are each configured to electrically contact the electrolyte solution 16. In an embodiment, the electrodes 42, 44 may be coupled via a sense resistor 46, and one electrode 44 may be connected to a relative ground 48. In such a configuration, a potential difference may be sensed by the potential detector 40 if there is a galvanic corrosion current passing through the solution.

The potential detector 40 may be coupled with a signal amplifier 50 that is configured to amplify the monitored electrical potential, and to provide a corresponding proportional output 52. The signal amplifier 50 may include a comparator, and or any necessary circuitry that may be required to provide the amplified signal. In an embodiment, such circuitry may provide internal feedback so the output 52 may track the detected input. As illustrated, the signal amplifier may be configured as an inverting amplifier if the signal provided by the potential detector 40 is expected to be negative. In an embodiment, the signal amplifier 50 may be a high impedance amplifier.

The signal amplifier 50 may be coupled with a corrosion indicator 60 configured to receive the output 52 of the signal amplifier 50 and provide an alert 62 if the output 52 is above a particular threshold. In an embodiment, the alert 62 may be used by a companion processor 64 and may indicate a needed service condition. For example, when the system 10 is used with metals having corrosion-resistant coatings, an alert 62 may indicate that the coating on a particular metal may have been compromised.

The output 52 from the signal amplifier 50 may also be provided to a current delivery circuit 70, which may be configured to provide a protective current 72 to the cathodic metal 14 in response to the sensed potential. The current delivery circuit 70 may include a power amplifier 74 operatively connected to the signal amplifier 50, and may be further coupled to a current delivery electrode 76 in electrical communication with the cathode 14. In an embodiment, the power amplifier 74 may provide an electrical current to the current delivery electrode 76 that is proportional to the output 52 of the signal amplifier 50.

During operation, if a potential is detected within the electrolyte solution 16 by the potential detector 40, the potential may be amplified by the signal amplifier 50 and current delivery circuit 70, and provided to the cathode 14 via the coupled current delivery electrode 76. By artificially supplying the cathode 14 with an external current 72 that is equal to the original galvanic corrosion current the cathode 14 may draw less (or no) current from the anode 12. By reducing the current draw from the anode 12, the system 10 will also reduce the corresponding corrosion of the anode 12 by slowing or stopping the flow of positive ions into the solution 16.

Figure 3:
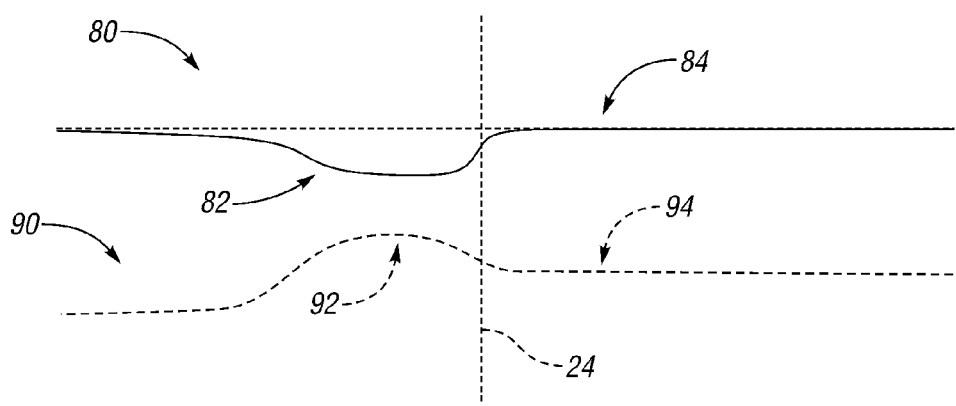
FIG. 3 is a current density plot and electrolyte solution potential plot across the anode and cathode illustrated in FIG. 1, in the presence of a protective current.

FIG. 3 illustrates a current density plot 80 of the metals 12, 14 shown in FIG. 1 when the current delivery circuit 70 is providing a current 72. As illustrated, the cathode 14 is still receiving current, as illustrated by the negative current density 82 left of the interface line 24; however, the anode 12 is not supplying any current, as illustrated by the generally zero current density 84 to the right of the interface 24. Instead, of being provided by the anode 12, as generally illustrated in FIG. 2, the current is being sourced directly from current delivery circuit 70 via the electrode 76. Similarly, in the electrical potential plot 90 of the electrolyte solution 16, the electrical potential 92 left of the interface 24 becomes much higher and the potential of the electrolyte 16 right of the interface 24 is generally flat 94. This flat nature is a result of the anode 12 neither supplying electrical current, nor providing positively charged ions to the solution 16.

In an embodiment, the signal amplifier 50 and current delivery circuit 70 may be configured in a negative feedback loop, together with the metals 12, 14, so that no electrical potential is present within the solution 16 adjacent the anode 12. As such, a sufficient amount of current may be provided by the current delivery circuit 70 to substantially negate the galvanic couple. Similarly, other control methods known in the art, such as, for example, integral control, may be incorporated within the current delivery circuit 70 to adjust the necessary amount of current.

Figure 4B:
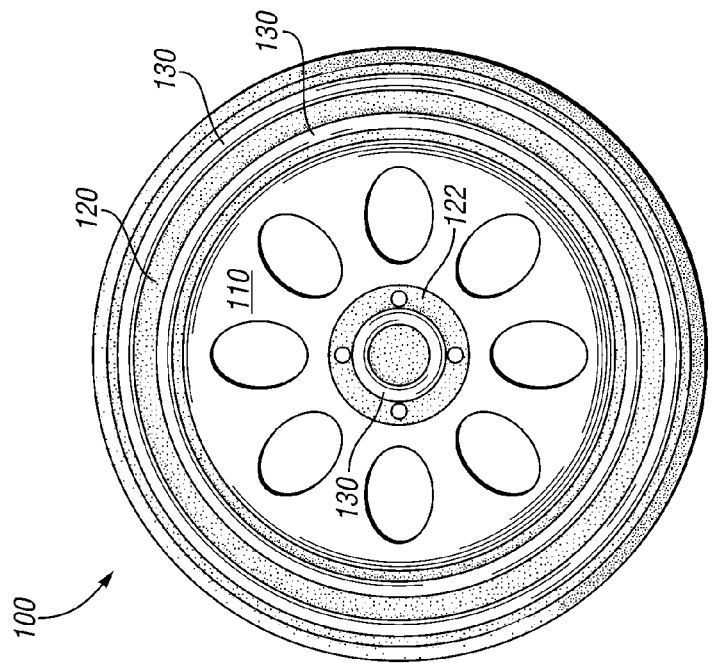
FIG. 4B is a schematic side view of the automotive wheel assembly shown in FIG. 4A.
Figure 4A:
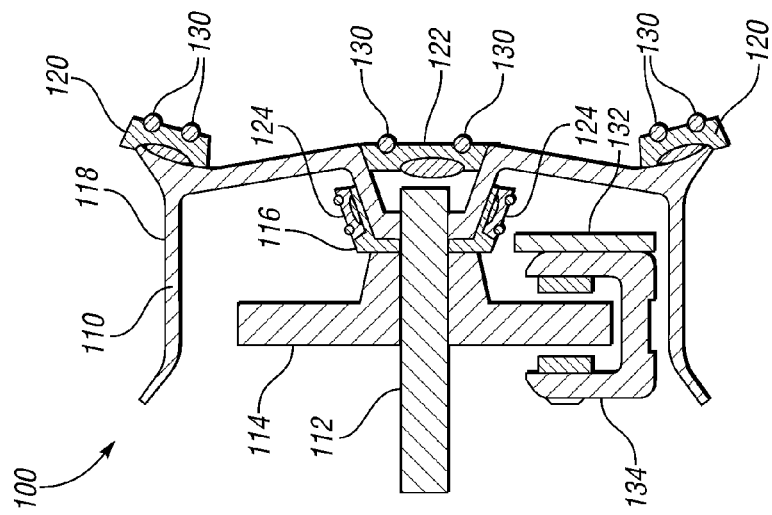
FIG. 4A is a schematic cross-sectional view of an automotive wheel assembly.

As illustrated in FIGS. 4A and 4B, the system for detecting and preventing galvanic corrosion of an anodic metal 12 may be used with an automotive vehicle wheel assembly 100. In an embodiment, the vehicle wheel 110 may be cast or machined from magnesium or a magnesium-based alloy—highly anodic materials on the Anodic Index. The wheel 110 may be coupled to a steel axle 112, steel bolts (not shown), and/or a steel brake disk 114. As generally understood, steel is considerably more "cathodic" on the Anodic Index than magnesium or certain magnesium alloys, and thus may have a tendency to cause the wheel to galvanically corrode.

To reduce the tendency for galvanic corrosion of the wheel assembly 100, the assembly 100 may further include an aluminum isolator 116, which may separate the magnesium wheel 110 from the various steel parts, and/or may include a corrosion resistant coating 118 over the surface of the wheel 110. As may be appreciated, during use, the vehicle wheel assembly 100 may be subjected to harsh environments that may include impacts with stones and/or other debris. These impacts may cause the corrosion resistant wheel coating 118 to chip and may expose the magnesium to the environment elements. Once exposed, water from the road may jointly coat the wheel 110 and other steel parts (e.g., axle 112 and/or brake disk 114), such as when the wheel assembly passes through a puddle. The water from the road may act as an electrolytic solution to provide an ionic pathway between the various parts, and may promote a galvanic couple between the exposed magnesium of the wheel 110 and the steel.

To detect the occurrence of galvanic corrosion, one or more potential detectors 120, 122, 124 may be provided around the wheel 110 in places where galvanic corrosion may be more likely to occur. For example, a first potential detector 120 may be positioned near the radial perimeter of the wheel 110, i.e., an area where stone chips in the protective wheel coating 118 may be more likely to occur. A second potential detector 122 may be located closer to the center hub, i.e., a place where the magnesium wheel 110 may directly interface with steel bolts (not shown). Other potential detectors (e.g., potential detector 124) may be located in other places of possible corrosion, such as, for example the aluminum isolator 116.

As illustrated, each potential detector may include one or more electrodes 130 that may be configured to electrically contact the electrolyte solution if such a solution is present. As described above, the potential detectors may be operative to sense a potential difference between pairs of electrodes 130. The sensed potential difference may be amplified by a signal amplifier (not shown), and a corresponding current may be provided to the steel ("cathodic") parts via a current delivery electrode 132. The electrode 132 may, for example, be coupled to a stationary part, such as the brake caliper 134, which may electrically transmit the protective current to the brake disk 114 and axle 112 when the brakes are applied.

Figure 5:
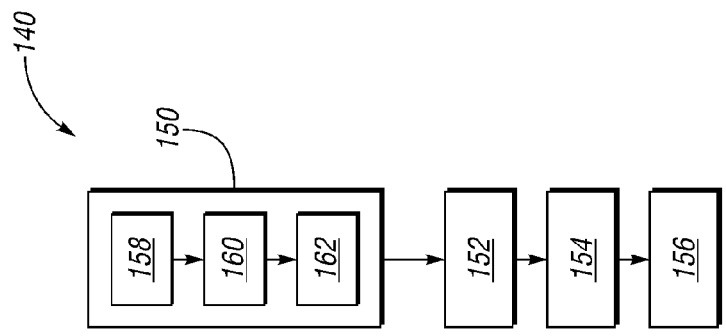
FIG. 5 is a schematic flow diagram of a method for detecting and preventing galvanic corrosion of an anodic metal.

FIG. 5 illustrates an exemplary method 140 of detecting and preventing galvanic corrosion of an anodic metal. In an embodiment, the method may be utilized when the anodic metal is provided in a galvanic couple with a cathodic metal and when exposed to an electrolyte solution. The method may include detecting an electrical potential within the electrolyte solution above a portion of the anodic metal (step 150), amplifying the detected electrical potential (step 152), and applying a current to the cathodic metal that is proportional to the amplified electrical potential (step 154).

The step of detecting an electrical potential within the electrolyte solution may further include providing a first electrode adjacent to the anodic metal (step 158), providing a second electrode adjacent to the anodic metal and apart from the first electrode (step 160), where the first and second electrodes are each configured to electrically contact the electrolyte solution, and detecting an electrical potential between the first and second electrodes (step 162). Finally, the method may also include providing an alert if the amplified electrical potential is above a threshold (step 156).

While the best modes for carrying out the invention have been described in detail, those familiar with the art to which this invention relates will recognize various alternative designs and embodiments for practicing the invention within the scope of the appended claims. All directional references (e.g., upper, lower, upward, downward, left, right, leftward, rightward, above, below, vertical, and horizontal) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not as limiting.

The invention claimed is:

1. A system for detecting and preventing galvanic corrosion of an anodic metal when coupled with a cathodic metal and exposed to an electrolyte solution, the system comprising:
   a potential detector configured to monitor an electrical potential within the electrolyte solution;
   a signal amplifier coupled with the potential detector, the signal amplifier configured to provide an output proportional to the monitored electrical potential; and
   a current delivery circuit coupled with the signal amplifier and configured to provide a current to the cathodic metal, the current being proportional to the output of the signal amplifier.

2. The system of claim 1, wherein the potential detector is disposed adjacent to the anodic metal.

3. The system of claim 1, wherein the potential detector includes a first and second electrode, each electrode configured to electrically contact the electrolyte solution; and
   wherein the potential detector is configured to detect an electrical potential between the first and second electrodes.

4. The system of claim 3, wherein the first electrode is disposed proximate an edge of the anodic metal next to the cathode.

5. The system of claim 3, wherein the second electrode is disposed more distant from the edge of the anodic metal than the first electrode.

6. The system of claim 1, wherein the signal amplifier is an inverting signal amplifier.

7. The system of claim 1, further comprising a corrosion indicator configured to receive the output of the signal amplifier and to provide an alert if the output is above a threshold.

8. The system of claim 1, wherein the current delivery circuit includes a power amplifier.

9. The system of claim 1, wherein the current delivery circuit includes a current delivery electrode that is electrically coupled with the cathodic metal.

10. The system of claim 1, wherein the system is operatively configured to detect corrosion of a magnesium-based vehicle wheel.

11. A method of detecting and preventing galvanic corrosion of an anodic metal when coupled with a cathodic metal and exposed to an electrolyte solution, the method comprising:
    detecting an electrical potential within the electrolyte solution above a portion of the anodic metal;
    amplifying the detected electrical potential; and
    applying a current to the cathodic metal that is proportional to the amplified electrical potential.

12. The method of claim 11, wherein detecting an electrical potential within the electrolyte solution comprises:
    providing a first electrode adjacent to the anodic metal;
    providing a second electrode above the anodic metal and apart from the first electrode, the first and second electrodes each being configured to electrically contact the electrolyte solution; and
    detecting an electrical potential between the first and second electrodes.

13. The method of claim 12, wherein the first electrode and second electrode are provided in a transverse arrangement to an interface between the anodic and cathodic metals.

14. The method of claim 11, further comprising providing an alert if the amplified electrical potential is above a threshold.

15. A system for detecting and preventing galvanic corrosion of magnesium vehicle wheel when provided in a galvanic couple with a cathodic metal and exposed to an electrolyte solution, the system comprising:
    a potential detector disposed over a portion of the wheel and configured to monitor an electrical potential within the electrolyte solution;
    a signal amplifier coupled with the potential detector, the signal amplifier configured to provide an output proportional to the monitored electrical potential; and
    a current delivery circuit coupled with the signal amplifier and configured to provide a current to the cathodic metal, the current being proportional to the output of the signal amplifier.

16. The system of claim 15, wherein the cathodic metal comprises a brake disk.

17. The system of claim 15, wherein the potential detector includes a first and second electrode, each electrode configured to electrically contact the electrolyte solution; and
    wherein the potential detector is configured to detect an electrical potential between the first and second electrodes.

18. The system of claim 15, further comprising a corrosion indicator configured to receive the output of the signal amplifier and to provide an alert if the output is above a threshold.

19. The system of claim 15, wherein the current delivery circuit includes a power amplifier.

20. The system of claim 15, wherein the potential detector is disposed proximate to the radial perimeter of the wheel.

* * * * *